US010561197B2

(12) United States Patent
Darby, II et al.

(10) Patent No.: US 10,561,197 B2
(45) Date of Patent: Feb. 18, 2020

(54) MEDICAL SHOE HAVING MULTI-DENSITY OVERMOLDING

(71) Applicant: DARCO INTERNATIONAL, INC., Huntington, WV (US)

(72) Inventors: H. Darrel Darby, II, Mount Pleasant, SC (US); Wu Zhang, Proctorville, OH (US)

(73) Assignee: DARCO INTERNATIONAL, INC., Huntington, WV (US)

( * ) Notice: Subject to any disclaimer, the term of this patent is extended or adjusted under 35 U.S.C. 154(b) by 0 days.

(21) Appl. No.: 15/559,656

(22) PCT Filed: Jun. 23, 2016

(86) PCT No.: PCT/US2016/038949
§ 371 (c)(1),
(2) Date: Sep. 19, 2017

(87) PCT Pub. No.: WO2017/222526
PCT Pub. Date: Dec. 28, 2017

(65) Prior Publication Data
US 2019/0116925 A1    Apr. 25, 2019

(51) Int. Cl.
*A43B 3/24* (2006.01)
*A43B 7/32* (2006.01)
(Continued)

(52) U.S. Cl.
CPC ............... *A43B 7/32* (2013.01); *A43B 3/128* (2013.01); *A43B 3/244* (2013.01); *A43B 7/1415* (2013.01);
(Continued)

(58) Field of Classification Search
CPC .......... A43B 3/24; A43B 3/244; A43B 13/36; A61F 5/0195
(Continued)

(56) References Cited

U.S. PATENT DOCUMENTS 3,538,628 A * 11/1970 Einstein, Jr. ......... A43B 3/0078
36/1
3,902,259 A * 9/1975 Cracco ................... A43B 3/103
36/101
(Continued)

FOREIGN PATENT DOCUMENTS

KR      20-0468794 Y1    9/2013
WO      2016/014828 A1   1/2016

OTHER PUBLICATIONS

Pending U.S. Appl. No. 15/559,623.
(Continued)

*Primary Examiner* — Marie D Bays
(74) *Attorney, Agent, or Firm* — Sughrue Mion, PLLC

(57) ABSTRACT

A medical shoe having an overmolding layer with a non-uniform density is provided. The medical shoe may include a midsole configured to support a foot, and a frame surrounding the midsole. The midsole may include a foot receiving portion forming a substantially planar surface for supporting the foot and a frame receiving portion opposite the foot receiving portion. The frame may include an overmolding layer extending from a side of the frame opposite the midsole so as to form a ground contacting surface. The overmolding layer may have a non-uniform density. The sole assembly may be secured to the frame by a self-locking fit between the sole assembly and the frame.

21 Claims, 14 Drawing Sheets

(51) Int. Cl.

| | | |
|---|---|---|
| A43B 11/00 | (2006.01) | |
| A43B 7/14 | (2006.01) | |
| A43B 7/20 | (2006.01) | |
| A43B 13/04 | (2006.01) | |
| A43B 13/18 | (2006.01) | |
| A43B 23/08 | (2006.01) | |
| A61F 5/01 | (2006.01) | |
| A43B 3/12 | (2006.01) | |
| A43B 13/36 | (2006.01) | |
| A43B 7/08 | (2006.01) | |
| A43C 11/06 | (2006.01) | |
| A43C 11/14 | (2006.01) | |

(52) U.S. Cl.
CPC .............. *A43B 7/20* (2013.01); *A43B 11/00* (2013.01); *A43B 13/04* (2013.01); *A43B 13/188* (2013.01); *A43B 13/36* (2013.01); *A43B 23/087* (2013.01); *A61F 5/0195* (2013.01); *A43B 7/085* (2013.01); *A43C 11/06* (2013.01); *A43C 11/1493* (2013.01)

(58) Field of Classification Search
USPC ........... 36/15, 110, 100, 101, 30 R, 31, 59 C
See application file for complete search history.

(56) References Cited

U.S. PATENT DOCUMENTS

| | | | |
|---|---|---|---|
| 4,179,826 A | 12/1979 | Davidson | |
| 4,255,874 A * | 3/1981 | Sironi | A43B 13/223 36/32 R |
| 4,267,650 A | 5/1981 | Bauer | |
| 4,314,412 A * | 2/1982 | Anderson | A43B 3/12 36/100 |
| 4,372,059 A * | 2/1983 | Ambrose | A43B 7/146 36/103 |
| 4,377,042 A | 3/1983 | Bauer | |
| 4,564,966 A * | 1/1986 | Chen | A43B 1/0027 12/146 B |
| 4,654,983 A * | 4/1987 | Graham | A43B 5/06 36/114 |
| 4,656,760 A | 4/1987 | Tonkel et al. | |
| 5,014,449 A * | 5/1991 | Richard | A43B 3/0084 36/114 |
| 5,067,256 A | 11/1991 | Darby | |
| 5,083,385 A | 1/1992 | Halford | |
| 5,317,822 A | 6/1994 | Johnson | |
| 5,329,705 A * | 7/1994 | Grim | A43B 1/0009 36/110 |
| 5,642,575 A * | 7/1997 | Norton | A43B 13/181 36/27 |
| 5,775,005 A | 7/1998 | McClelland | |
| 5,799,417 A | 9/1998 | Burke et al. | |
| 6,038,790 A * | 3/2000 | Pyle | A43B 7/1425 36/28 |
| 6,345,454 B1 | 2/2002 | Cotton | |
| 6,915,596 B2 * | 7/2005 | Grove | A43B 13/223 36/100 |
| 6,931,766 B2 | 8/2005 | Greene | |
| 7,140,129 B2 | 11/2006 | Newson et al. | |
| 7,793,429 B2 * | 9/2010 | Ellis, III | A43B 3/0005 36/100 |
| 7,946,059 B2 * | 5/2011 | Borel | A43B 13/026 36/28 |
| 7,966,748 B2 * | 6/2011 | Votolato | A43C 15/02 36/100 |
| 8,020,318 B2 * | 9/2011 | Khalifa | A43B 1/0027 36/100 |
| 8,225,532 B2 * | 7/2012 | Chen | A43B 1/0009 36/103 |
| 8,291,619 B2 * | 10/2012 | Abadjian | A43B 5/00 36/113 |
| 8,474,155 B2 | 7/2013 | McDonald et al. | |
| 2002/0050079 A1 * | 5/2002 | Yoshiaki | A43B 13/125 36/132 |
| 2002/0073578 A1 * | 6/2002 | Ellis, III | A43B 5/00 36/25 R |
| 2003/0046832 A1 * | 3/2003 | Knoerr | A43B 1/0027 36/30 R |
| 2003/0196353 A1 * | 10/2003 | Baek | A43B 7/1425 36/113 |
| 2004/0194351 A1 * | 10/2004 | Gallegos | A43B 3/24 36/140 |
| 2004/0255486 A1 * | 12/2004 | Pawlus | A43B 3/0047 36/10 |
| 2005/0172517 A1 * | 8/2005 | Bledsoe | A43B 7/141 36/110 |
| 2005/0188562 A1 * | 9/2005 | Clarke | A43B 5/18 36/15 |
| 2005/0268490 A1 * | 12/2005 | Foxen | A43B 7/1425 36/28 |
| 2006/0137221 A1 | 6/2006 | Dojan et al. | |
| 2007/0017124 A1 * | 1/2007 | Koo | A43B 13/02 36/59 R |
| 2007/0186446 A1 * | 8/2007 | Lafortune | A43B 7/142 36/43 |
| 2007/0240338 A1 * | 10/2007 | Din Mahamed | A43B 9/10 36/25 R |
| 2007/0245504 A1 | 10/2007 | Spector | |
| 2008/0000108 A1 * | 1/2008 | Ellis, III | A43B 3/0005 36/113 |
| 2008/0047167 A1 | 2/2008 | Pawl us et al. | |
| 2008/0141565 A1 | 6/2008 | Rini et al. | |
| 2009/0071041 A1 | 3/2009 | Hooper | |
| 2009/0126230 A1 | 5/2009 | McDonald et al. | |
| 2009/0320329 A1 | 12/2009 | Darby, II et al. | |
| 2010/0146819 A1 * | 6/2010 | Teteriatnikov | A43B 13/145 36/103 |
| 2010/0170114 A1 * | 7/2010 | Jara | A43B 1/0009 36/114 |
| 2010/0275471 A1 * | 11/2010 | Teteriatnikov | A43B 13/145 36/30 R |
| 2010/0324461 A1 | 12/2010 | Darby, II et al. | |
| 2011/0283560 A1 * | 11/2011 | Portzline | A43B 13/04 36/31 |
| 2012/0073160 A1 | 3/2012 | Marvin et al. | |
| 2012/0180344 A1 * | 7/2012 | Crowley, II | A43B 1/0009 36/32 R |
| 2012/0317845 A1 * | 12/2012 | Vattes | A43B 7/141 36/30 R |
| 2013/0160331 A1 | 6/2013 | Burke et al. | |
| 2013/0269213 A1 | 10/2013 | Gift et al. | |
| 2014/0276317 A1 | 9/2014 | Batterson et al. | |
| 2015/0181976 A1 * | 7/2015 | Cooper | A43B 13/187 36/28 |
| 2016/0045354 A1 | 2/2016 | Lee et al. | |

OTHER PUBLICATIONS

Communication dated Apr. 10, 2019 from the United States Patent and Trademark Office in U.S. Appl. No. 15/559,656.

Communication dated Jul. 29, 2019 from the United States Patent and Trademark Office in U.S. Appl. No. 15/559,656.

Communication dated Jun. 19, 2019, from the European patent Office in application No. 16906451.6.

Communication dated Jul. 9, 2019, from the European Patent Office in application No. 16906451.6.

International Search Report of PCT/US2016/038958 dated Oct. 28, 2016 [PCT/ISA/210].

Written Opinion of PCT/US2016/038958 dated Oct. 28, 2016 [PCT/ISA/237].

Communication dated Aug. 23, 2019 from the United States Patent and Trademark Office in U.S. Appl. No. 15/559,623.

Communication dated Jun. 7, 2019, from the European Patent Office in application No. 16906449.0.

Communication dated Jun. 21, 2019, from the European Patent Office in counterpart application No. 16906449.0.

(56) References Cited

OTHER PUBLICATIONS

International Search Report for PCT/US/2016/038949 dated Sep. 14, 2016 [PCT/ISA/210].
Written Opinion for PCT/US/2016/038949 dated Sep. 14, 2016 [PCT/ISA/237].

* cited by examiner

MEDICAL SHOE HAVING MULTI-DENSITY OVERMOLDING

BACKGROUND

1. Field

Apparatuses and methods consistent with the present disclosure relate to a medical shoe for supporting a post-operative or otherwise traumatized patient's foot, and more particularly to a surgical shoe having a multi-density overmolding configured to provide a customized weight distribution across a patient's foot. For example, the multi-density overmolding may be configured to offload pressure at a location of a wound or other traumatized area of the patient's foot.

2. Description of the Related Art

Medical shoes play an essential role in recovery following surgery or other trauma to a patient's foot. For instance, the medical shoe may assist in redistributing weight away from the wound or traumatized area, such that the wound or traumatized area may heal.

However, such medical shoes may be prohibitively expensive, as they often require labor intensive manufacturing steps including gluing and stitching. Additionally, these manufacturing steps are often susceptible to failure, and frequently result in shortening the usable life of the medical shoe.

As a result, there are no suitable post-trauma medical shoes that effectively redistribute weight away from a wound or traumatized area of a patient's foot without requiring labor intensive manufacturing methods including gluing and stitching to assemble the medical shoe.

There is therefore a need to provide a post-trauma medical shoe that does not require labor intensive and failure prone manufacturing methods including gluing and/or stitching (or minimizes the same), designed to be used by patients who have experienced either surgery of the foot, trauma to the foot, or have foot pain aggravated by weight bearing such as heel spur syndrome, plantar fasciitis, calcinosis, Achilles tendonitis, or have skin lesions, ulcers or infections of the foot area where reduction of weight would enhance the healing process and allow the patient to be ambulatory.

SUMMARY

According to an aspect of an exemplary embodiment, a medical shoe includes a midsole configured to support a foot, the midsole including a foot receiving portion forming a substantially planar surface for supporting the foot; and a frame receiving portion opposite the foot receiving portion; a frame surrounding the midsole, the frame including a plurality of through holes, and an overmolding layer extending from a side of the frame opposite the midsole so as to form a ground contacting surface, wherein the overmolding layer has a non-uniform density, and wherein the midsole is secured to the frame by a self-locking fit between the midsole and the frame.

The midsole may further include a midsole lip portion extending around a circumferential edge of the midsole in a direction perpendicular to the substantially planar surface, the frame may further include a frame lip portion surrounding the midsole lip portion such that a contour of an inner surface the frame lip portion corresponds to a contour of an outer surface the midsole lip portion, and the self-locking fit may include a frictional force between the midsole and the frame.

The midsole may further include a fixation projection extending from the midsole lip portion in a direction parallel to the substantially planar surface, the frame may further include a fixation projection through hole in the frame lip portion, and the fixation projection may extend into the fixation projection through hole.

The overmolding layer may include a rear heel portion, a midfoot portion, and a front forefoot portion; the front forefoot portion may have a first density; the rear heel portion may have a second density different than the first density; and the midfoot portion may have a third density equal to one of the first density and the second density.

The first density may be greater than the second density. The second density may be greater than the first density. The midsole may include ethylene-vinyl acetate. The overmolding layer may include a tread pattern formed therein on the ground contacting surface.

The medical shoe may further include a removable cover secured to the frame and located above the midsole, such that a cavity configured to surround the foot is defined by a bottom surface of the removable cover and a top surface of the midsole.

The medical shoe may further include a fixation element and a closure strap, wherein the fixation element is secured to a fixation projection extending from the frame and includes a fixation element slot configured to receive the closure strap; the removable cover may include a removable cover slot configured to receive the closure strap, and the closure strap may be positioned through the fixation element slot and through the removable cover slot. Ventilation holes may be formed in the removable cover.

The medical shoe may further include a removable insole located on the substantially planar surface, the removable insole including a foot supporting portion; and a plurality of pressure distribution pegs extending from the food supporting portion towards the substantially planar surface, wherein the plurality of pressure distribution pegs are non-uniform in height.

According to an aspect of an exemplary embodiment, a snap fit medical shoe assembly includes a midsole configured to support a foot, the midsole including a foot receiving portion forming a substantially planar surface for supporting the foot; a frame receiving portion opposite the foot receiving portion; and a midsole lip portion extending around a circumferential edge of the midsole in a direction perpendicular to the substantially planar surface; a rigid exoskeleton configured to surround the midsole, the rigid exoskeleton including an exoskeleton lip portion corresponding to the midsole lip portion; and an ethylene-vinyl acetate overmolding layer extending from a side of the rigid exoskeleton opposite the midsole so as to form a ground contacting surface; and a removable cover configured to be secured to the rigid exoskeleton, wherein the ethylene-vinyl acetate overmolding layer has a non-uniform density, and wherein a contour of an inner surface the exoskeleton lip portion corresponds to a contour of an outer surface the midsole lip portion, such that the midsole is configured to be secured to the rigid exoskeleton by a snap fit between the midsole and the rigid exoskeleton.

The ethylene-vinyl acetate overmolding layer may include a rear heel portion, a midfoot portion, and a front forefoot portion; the front forefoot portion may have a first density; the rear heel portion may have a second density different than the first density; and the midfoot portion may have a third density equal to one of the first density and the second density. The first density may be greater than the second density. The second density may be greater than the first density.

According to an aspect of an exemplary embodiment, a method of attaching orthopedic bracing includes providing a midsole configured to support a foot of a patient, the midsole including a foot receiving portion forming a substantially planar surface for supporting the foot; and a frame receiving portion opposite the foot receiving portion, providing a rigid exoskeleton, the rigid exoskeleton including an overmolding layer having a non-uniform density, positioning the midsole into an interior of the rigid exoskeleton such that the midsole is secured to the rigid exoskeleton by a snap fit between the midsole and the rigid exoskeleton; positioning the substantially planar surface adjacent to a bottom portion of the foot of the patient; and positioning a removable cover adjacent to a top portion of the foot of the patient foot and securing the removable cover to the rigid exoskeleton.

The providing the midsole may include providing a midsole based on data of the foot of the patient, such that the non-uniform density corresponds to a medical condition of the patient. The providing the rigid exoskeleton may include providing a rigid exoskeleton not based on the data of the foot of the patient. The medical condition of the patient may be one of surgery of the foot, trauma of the foot, a wound of the foot, and an ulceration of the foot.

BRIEF DESCRIPTION OF THE DRAWINGS

These and/or other aspects will become apparent and more readily appreciated from the following description of the exemplary embodiments, taken in conjunction with the accompanying drawings, in which.

DETAILED DESCRIPTION

Merits and features of the present disclosure, and a method for accomplishing the merits and features, will become apparent upon reference to the exemplary embodiments described below with the accompanying drawings. However, the present disclosure may be embodied in many different forms and should not be construed as being limited to the embodiments set forth herein. Rather, these embodiments are provided so that this disclosure will be thorough and complete, and will fully convey the concept of the disclosure to those of ordinary skill in the art. The scope of the disclosure is defined only by the claims.

Figure 1:
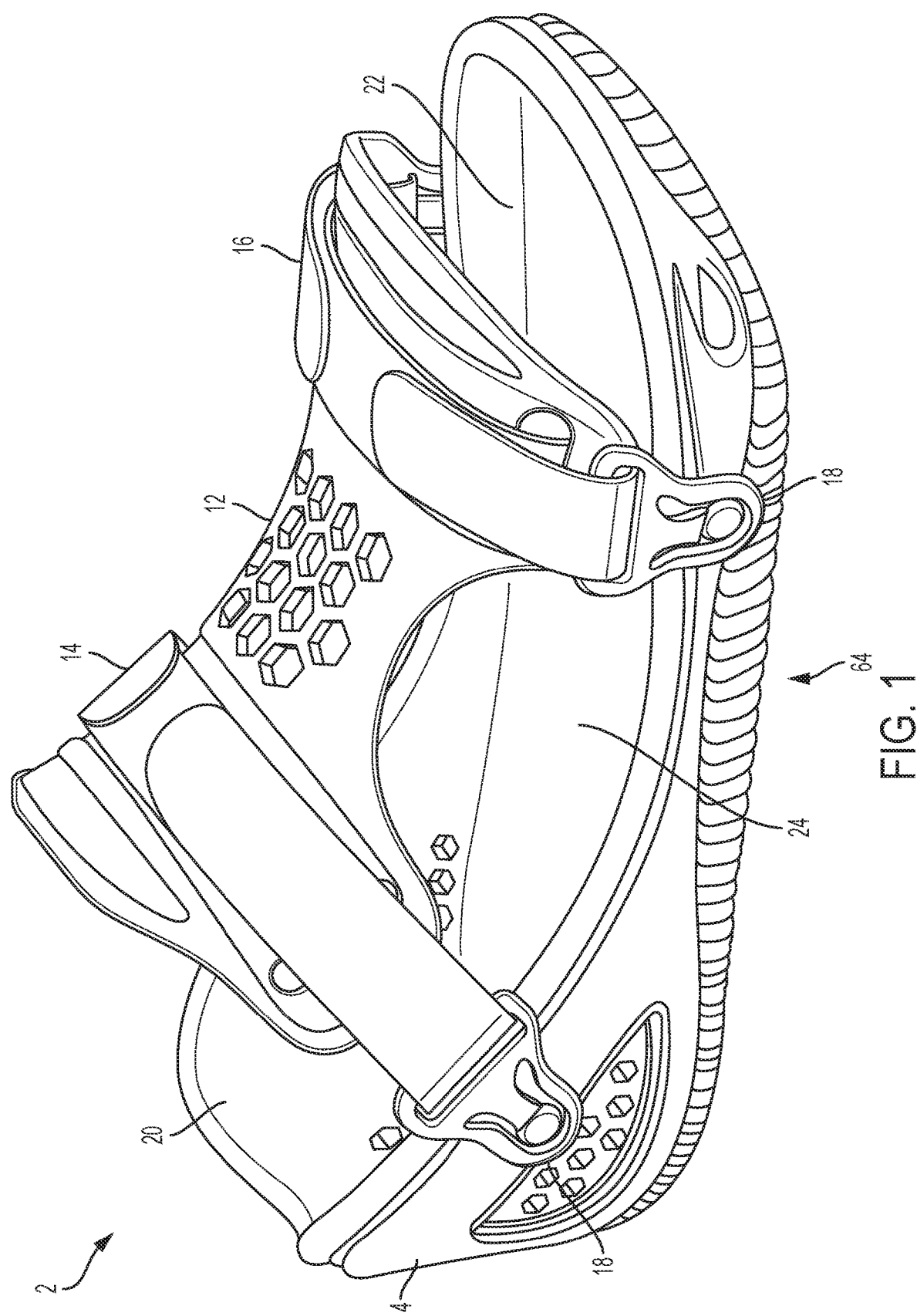
FIG. 1 is a side view of a medical shoe according to an aspect of an exemplary embodiment.
Figure 2:
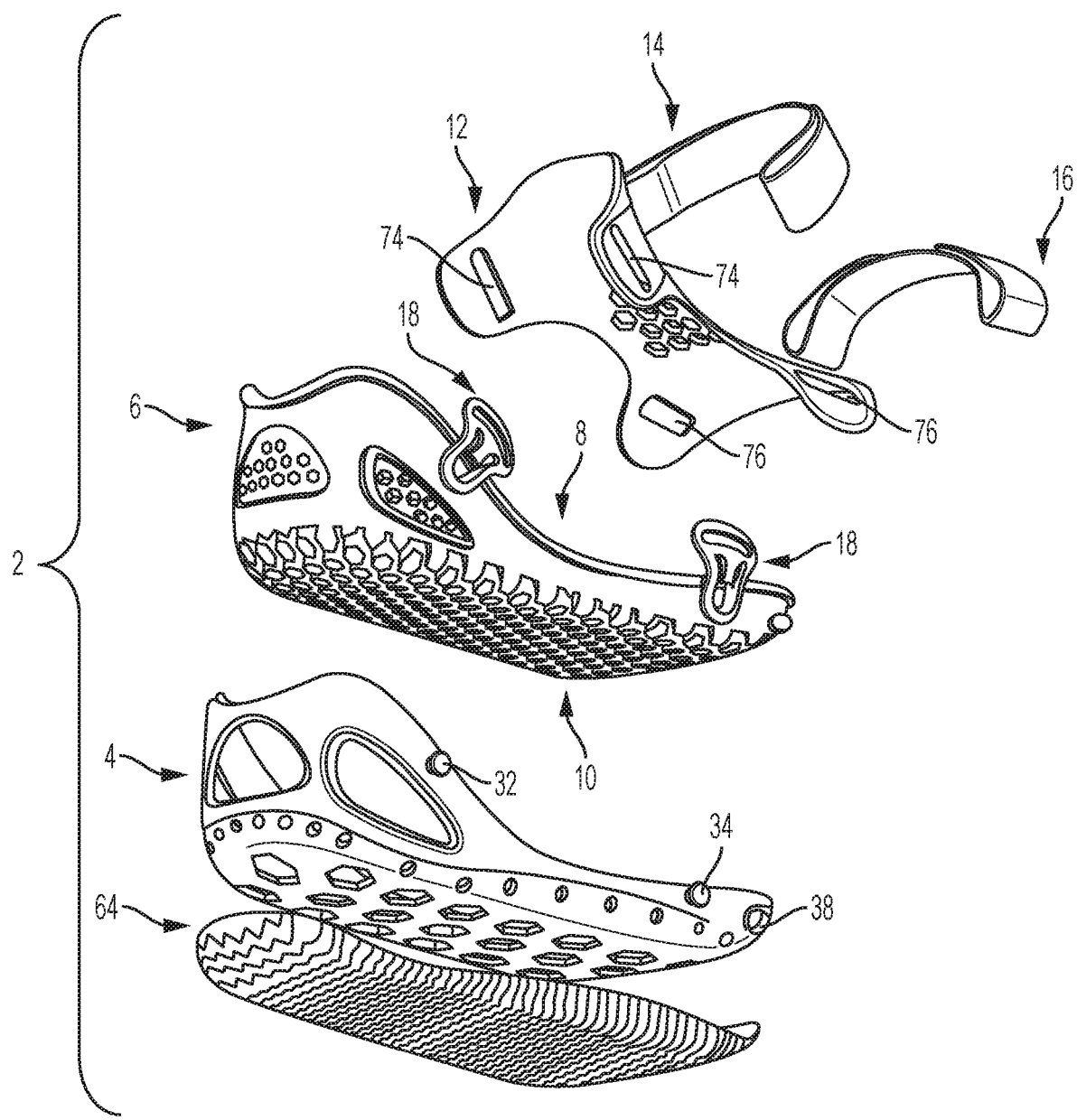
FIG. 2 is an exploded side elevation view of a medical shoe according to an aspect of an exemplary embodiment.

FIG. 1 is a side view of a medical shoe according to an aspect of an exemplary embodiment. FIG. 2 is an exploded side elevation view of a medical shoe according to an aspect of an exemplary embodiment.

A medical shoe 2 according to an aspect of an exemplary embodiment includes a frame 4, a midsole 6, and a removable cover 12. The frame 4, midsole 6, and removable cover 12 are separable from each other, and are not integrally formed with one another.

The frame 4 is made of a lightweight material and acts as a rigid exoskeleton outside the midsole 6. For instance, the frame 4 has a concave interior portion configured to receive the midsole 6 so that the midsole 6 may be inserted into frame 4. Once midsole 6 is inserted into the frame 4, the frame 4 surrounds an exterior circumference of the midsole 6, for instance to form a protective barrier around the midsole 6.

The midsole 6 is an insert for inserting into the frame 4 and includes a foot receiving portion 8 and a frame receiving portion 10 (see FIG. 2) that are integrally formed with one another. In other words, the midsole 6 may be a single piece comprising the foot receiving portion 8 and the frame receiving portion 10. The foot receiving portion 8 defines a top portion of the midsole 6 and includes a foot bed area for contacting and/or supporting a patient's foot. The frame receiving portion 10 defines a bottom portion of the midsole 6 and is received into and is surrounded by the frame 4.

The frame 4 and the midsole 6 are configured to establish a self-locking fit, for instance a snap fit, when the midsole 6 is inserted into the frame 4. For instance, as discussed in more detail below, the peripheral shape of the midsole 6 may correspond to the peripheral shape of the frame 4 such that the midsole 6 is received into the frame 4 and the self-locking fit can be established. Additionally, or in the alternative, fixation projections of the midsole 6 may be fit into corresponding holes in the frame 4 to reinforce and secure the self-locking fit between the midsole 6 and the frame 4. Once the self-locking fit is engaged between the frame 4 and the midsole 6 (for instance, as in the configuration shown in FIG. 1), the self-locking fit can be disengaged by separating the midsole 6 from the frame 4. This can be done by force, for instance by pulling the frame 4 and the midsole 6 in opposite directions.

The frame 4 and the midsole 6 may be fully self-locking, such that glue and stitching is not required. In other words, the frame 4 and the midsole 6 can be secured without gluing or stitching, and the self-locking fit may be sufficient to secure the frame 4 to the midsole 6 for use by a patient. Once the self-locking fit between the frame 4 and the midsole 6 is established, a force of friction between the frame 4 and the midsole 6 holds the frame 4 and the midsole 6 in mutual contact.

As will be discussed later, additional features may be provided to maintain the self-locking fit between the frame 4 and the midsole 6. For instance, the midsole 6 may include a projection extending from the midsole portion 8 in a substantially horizontal direction. The projection may be received into a corresponding through hole in the frame 4 in order to establish or maintain the self-locking fit between the frame 4 and the midsole 6.

An overmolding layer 64 is fixed to a bottom surface of the frame 4 opposite the midsole 6 and configured to extend from the frame 4 so as to form a ground contacting surface of the medical shoe 2. For instance, the overmolding layer 64 may be configured to absorb impact of the patient's foot while walking or running in the medical shoe 2. During a foot strike, the overmolding layer 64 may be compress on impact, and then may expand back to its original shape once the patient's foot is lifted.

The overmolding layer 64 may be made of foam plastic polymers, including synthetic or semi-synthetic materials. For instance, the overmolding layer may be made of ethylene-vinyl acetate (EVA) foam. EVA has the benefits of low-temperature toughness, stress-crack resistance, waterproof properties, and resistance to UV-radiation. Additionally, or in the alternative, the overmolding layer 64 may be made of polyurethane. For instance, a blend of EVA and polyurethane may be used.

As shown in FIG. 2, the removable cover 12 forms a top portion of the medical shoe 2. The removable cover 12 is easily secured to and detached from the frame 4 using a first closure strap 14 and a second closure strap 16. The first closure strap 14 and the second closure strap 16 are able to secure the cover 12 in place in a position above the midsole 6.

The first closure strap 14 and the second closure strap 16 may be fastening belts or bands that extend across the face of the removable cover 12, opposite the frame 4 and midsole 6, and thus exert a downward force on the removable cover 12 towards the frame 4 and midsole 6. The first closure strap 14 and the second closure 16 are oriented on opposite ends of the removable cover 12 (such that the first closure strap 14 is near the patient's ankle and the second closure strap 16 is near the patient's toes, for example). The first closure strap 14 and the second closure strap 16 may be laces for tying, or may include self-engaging hook and loops. The first closure strap 14 and the second closure strap 16 may be fully adjustable, so that the removable cover 12 may be adjusted with respect to the frame 4 and midsole 6.

The first closure strap 14 and the second closure strap 16 are secured to the frame 4 by one or more fixation elements 18. The embodiment shown in FIG. 2 shows one fixation element for each strap. That is, fixation element 18 is secured to the frame 4 and receives one of the first closure strap 14 or the second closure strap 16. The structure and attachment of fixation element 18 to the frame 4 is discussed in more detail below.

Once the removable cover 12 is secured to the frame 4, a cavity is defined between the foot receiving portion 8 of the midsole 6 and the removable cover 12 for housing and protecting a foot. As shown in FIG. 1, the cavity includes an ankle opening 20 in a rear area of the medical shoe 2 (i.e. near the patient's ankle), a forefoot opening 22 opposite the ankle opening 20 in a front area of the medical shoe 2 (i.e. near the patient's toes), and a midfoot opening 24 in between the ankle opening 20 and the forefoot opening 22 in a central area of the medical shoe 2. These openings, particularly the forefoot opening 22 and the midfoot opening 24, allow the patient or another person, such as a medical professional, to access the protected foot without removing the medical shoe 2.

The cavity may be configured to receive a foot after the removable cover 12 is secured to the frame 4. In the alternative, the removable cover 12 may be configured to be secured to the frame 4 after a foot has been received into the foot receiving portion 8.

Figure 3:
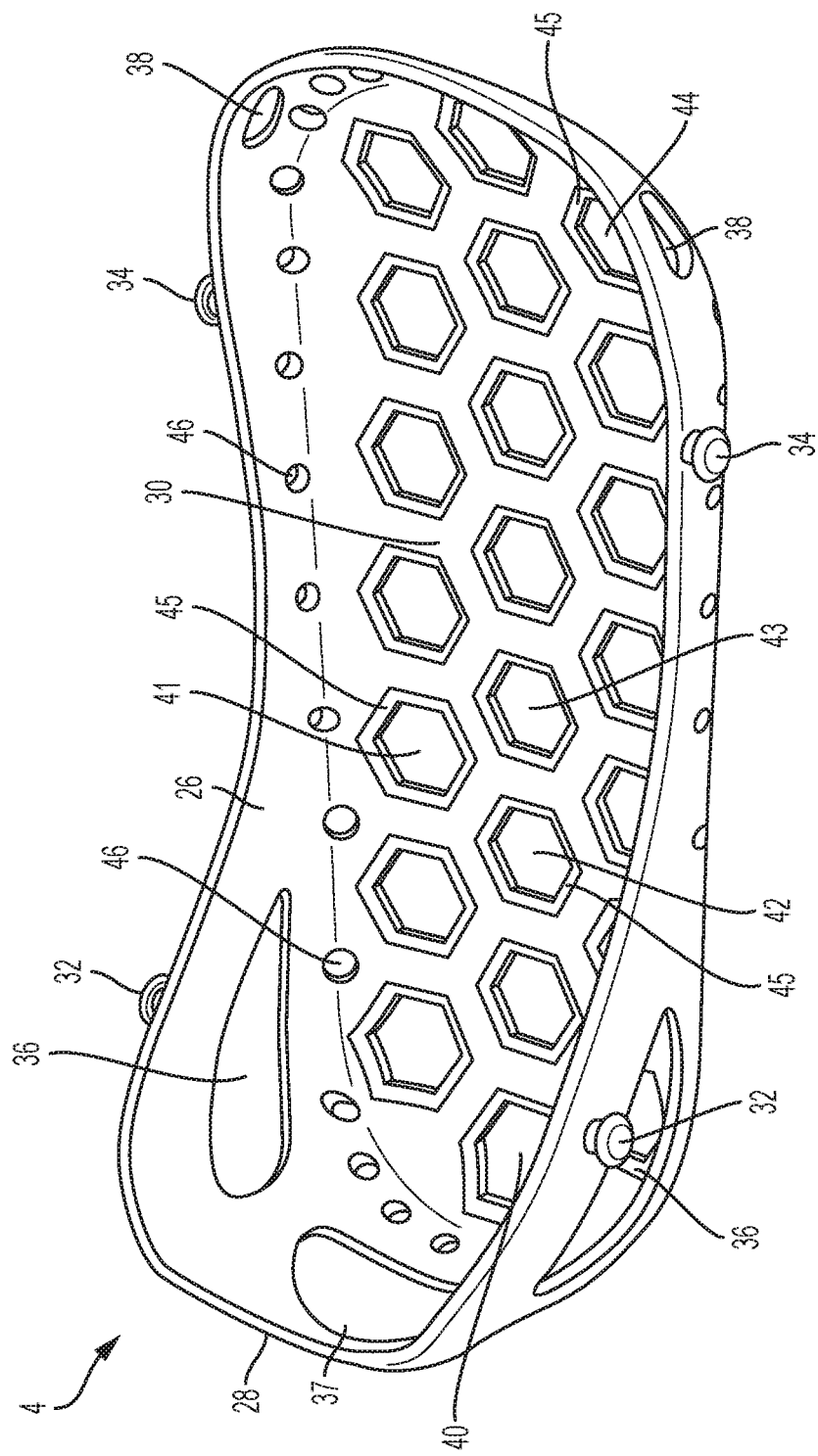
FIG. 3 is a side elevation view of a frame according to an aspect of an exemplary embodiment.

FIG. 3 is a side elevation view of a frame according to an aspect of an exemplary embodiment.

The frame 4 includes a frame lip 26, a frame lip heel portion 28, and a frame web portion 30. The frame web portion 30 is a planar surface of the frame 4 that is parallel or substantially parallel with a planar surface of the foot receiving portion 8 of the midsole 6 when the midsole 6 is inserted into the frame 4. The frame lip 26 extends around the edge of the frame web portion 30 in a direction perpendicular to the frame web portion 30, so as to define an outer perimeter of the foot bed and/or to create a wall around the medical shoe 2. For instance, the frame web portion 30 extends in a horizontal plane, while the frame lip 26 extends in a vertical plane around the frame web portion 30.

The frame lip heel portion 28 is an extended portion of the frame lip 26 adjacent to a rear heel area of the midsole 6 below the ankle opening 20 of the assembled medical shoe 2. For instance, the frame lip heel portion 28 defines a back wall for supporting the patient's heel and extends further from the frame web portion 30 than the remainder of the frame lip 26. Thus, the frame lip heel portion 28 may provide added support to a rear area of the patient's foot or ankle when the patient's foot is inserted into the medical shoe 2.

The frame lip 26 includes fixation projections 32 and 34 that allow fixation elements 18, for example, of the medical shoe 2 to be secured to the frame 4. The fixation projections 32 and 34 extend from the frame lip 26 in a substantially horizontal direction parallel or substantially parallel with the frame web portion 30. Rear fixation projections 32 are located on both sides of a rear area of the frame lip 26, i.e., on opposing sides of the frame lip heel portion 28. The rear fixation projections 32 are provided on the frame lip heel portion 28 and thus are displaced further from the frame web portion 30 in a vertical direction than front fixation projections 34. Front fixation projections 34 are located on both sides of a front area of the frame lip 26. Thus, fixation projections 32 and 34 are located on opposing sides of the frame 4 at both the rear and front areas, for a total of four fixation projections extending from the frame 4. However, any number of fixation projections may be provided, and the fixation projections 32 and 34 may be located at any position on the frame 4.

The frame lip 26 may include one or more holes 36, 37, and 38 formed therein. As shown in FIG. 3, the frame lip heel portion 28 includes two side ventilation holes 36 and a center ventilation hole 37. The center ventilation hole 37 is centrally located in the frame lip heel portion 28 and corresponds to the rear or back side of the frame 4. The side ventilation holes 36 are symmetrically provided on either side of the center ventilation hole 37.

The frame 4 further includes side projection holes 38 formed in the frame lip 26 that are used to secure other elements to frame 4. As shown in FIG. 3, side projection holes 38 are provided in the frame lip 26 on opposite sides of the front area of the frame 4. However, the side projection holes 38 may be provided at any location of the frame lip 26, including the central area of the frame lip 26 and the rear area of the frame lip 26.

The frame 4 further includes a plurality of frame holes 40, 41, 42, 43, and 44 formed in the frame web portion 30. For instance, a heel frame hole 40 may be formed in a rear portion of the frame web portion 30 adjacent to the frame lip heel portion 28. Midfoot frame holes 41, 42, and 43 may be formed in a central portion of the frame web portion 30 between the rear area and the front area of the frame web portion 30. Forefoot frame hole 44 may be formed in a front area of the frame web portion 30. The projection through holes may be symmetrically oriented with respect to the central axis of the web portion 30. Each frame hole 40, 41, 42, 43, and 44 may be circumscribed by a frame hole depression 45 around its border. For instance, the frame hole depression 45 may be a recessed area that traverses the circumference of the frame hole. The frame 4 may further include one or more side frame holes 46. The side frame holes may be located in the frame lip 26, or at the interface between the frame lip 26 and the frame web portion 30. The frame holes 40, 41, 42, 43, and 44 and the side frame hole 46 may support the self-locking or snap fit between the frame 4 and the midsole 6. The frame holes 40, 41, 42, 43, and 44 and the side frame hole 46 may also support adhesion between the frame 4 and the overmolding layer 64.

The frame 4 may be made of any light weight rigid material such that the frame 4 provides a form shaping exoskeleton for the medical shoe 2. For instance, the frame 4 may be made of a thermoplastic including polyethylene, polypropylene, polystyrene and polyvinyl chloride. The frame may also be made by a thermoset polymer including polyurethane.

Figure 4A:
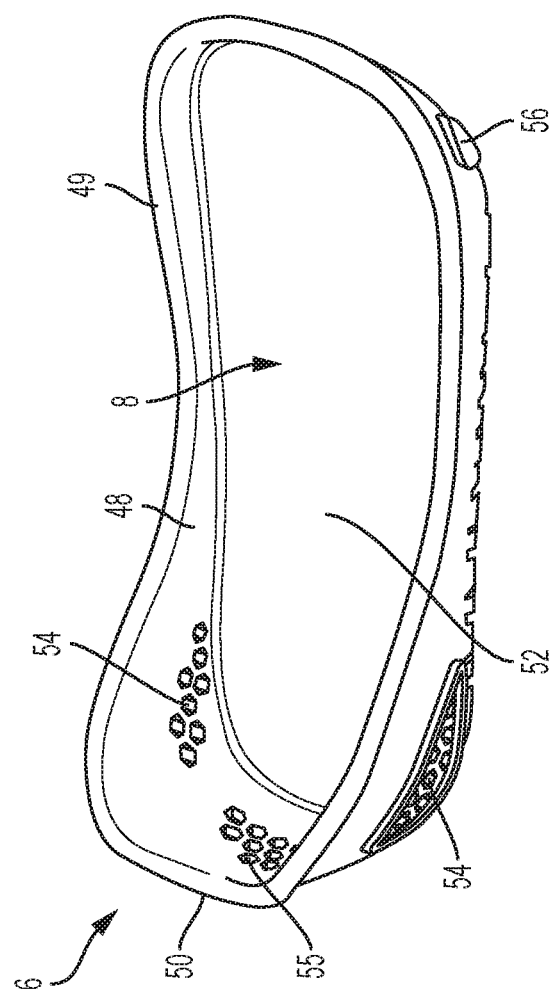
FIGS. 4A and 4B are side views of a midsole according to an aspect of an exemplary embodiment.
Figure 4B:
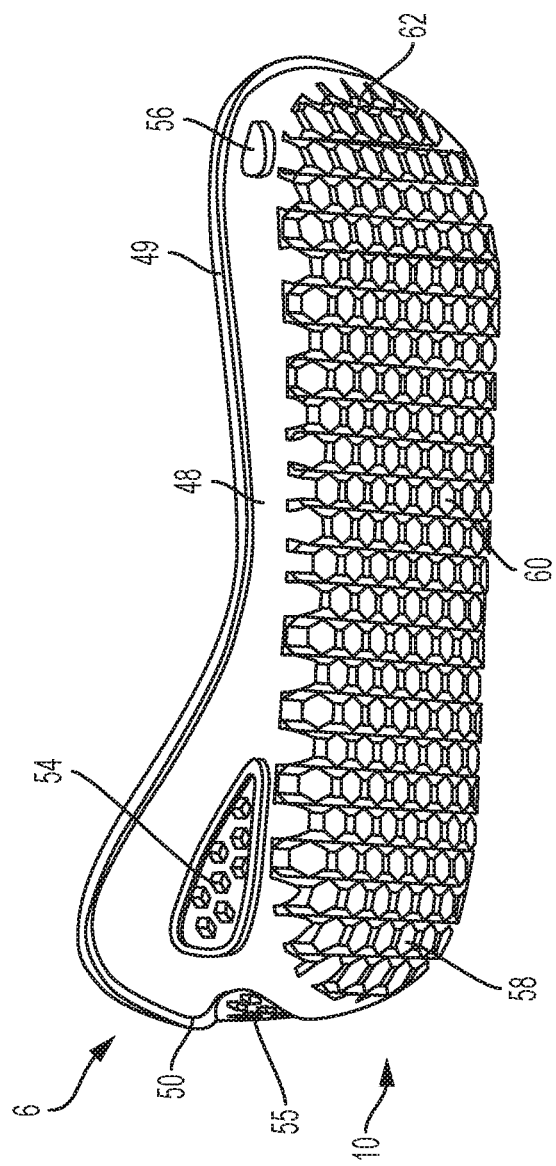

FIGS. 4A and 4B are side elevation views of a midsole according to an aspect of an exemplary embodiment.

The midsole 6 includes the foot receiving portion 8 on the top side of the midsole 6 and the frame receiving portion 10 on the bottom of the midsole 6. The foot receiving portion 8 defines the foot bed configured to receive the patient's foot and to be positioned within the frame 4 in the medical shoe 2 once assembled. The midsole 6 defines a rear heel area configured to receive the patient's heel and positioned adjacent to the ankle opening 20 when the medical shoe 2 is assembled. The midsole 6 further includes a front forefoot area configured to receive the patients forefoot positioned adjacent to the forefoot opening 22 when the medical shoe 2 is assembled. The midsole 6 also includes a midfoot area configured to receive the patient's midfoot positioned adjacent to the midfoot opening 24 when the medical shoe 2 is assembled.

The foot receiving portion 8 includes a planar foot supporting portion 52 and a midsole lip 48 circumferentially provided around the edge of the foot supporting portion 52. The midsole lip 48 extends in a direction substantially perpendicular to the foot supporting portion 52 so as to create a wall around the edge of the foot supporting portion 52. As shown in FIG. 4A, the midsole lip 48 may create a square forefoot design to act as a bumper to protect the patient's forefoot and to provide a better universal left/right fit.

The midsole lip 48 includes a midsole lip rib 49 and a midsole lip heel portion 50. The midsole lip rib 49 is a rib or raised band extending around the top edge of the midsole lip 48. The midsole lip rib 49 may assist in positioning or seating the midsole 6 into the frame 4. For instance, the midsole lip rib 49 may be positioned so as to act as a bumper or stopper and to stop the midsole 6 from being inserted farther into the frame 4 once the midsole 6 is properly seated in the frame 4. When the midsole 6 is inserted into the frame 4, the midsole lip rib 49 may come into contact with the frame lip 28, indicating that the midsole 6 is properly seated in the frame 4.

The midsole lip 48 further includes the midsole lip heel portion 50 at the rear area of the midsole 6. The midsole lip heel portion 50 extends further away from the foot supporting portion 52 than the remainder of the midsole lip 48, thus defining a heightened back wall for the patient's heel. The midsole lip heel portion 50 may provide additional support to the patient's heel and ankle when the patient's foot is inserted into the midsole 6.

The foot supporting portion 52 is generally or substantially planar, and is shaped to receive and support the patient's foot. In other words, although the foot supporting portion 52 is generally flat and extends along a horizontal plane, the foot supporting portion 52 may be curved to correspond to certain contours of the patient's foot. The curvature may include a raised portion in midfoot area of the foot supporting portion 52, for instance to provide additional support to the arches of the patient's foot. The front forefoot area of the foot supporting portion 52 may also include an upward curvature for supporting the patient's forefoot. In the alternative, the foot supporting portion 52 may be flat so as to receive a removable insole.

The midsole lip 48 may include a plurality of ventilation holes 54 and 55 formed in the midsole lip 48 that provide ventilation to the patient's foot. Side ventilation portions 54 are formed on either side of center ventilation portion 55 in the midsole lip heel portion 50 of the midsole lip 48. For instance, when the midsole 6 is inserted into the frame 4, the ventilation portions 54 and 55 in the midsole 6 are aligned with the ventilation holes 36 and 37 in the frame lip 26. Thus, when assembled, the medical shoe 2 has uninterrupted ventilation holes providing a ventilating current of air to the patient's foot.

Fixation projections 56 are provided on opposing sides on the front area of the midsole lip 48. The fixation projections 56 extend from the midsole lip 48 in a direction substantially perpendicular to the midsole lip 48, i.e., parallel to the foot supporting portion 52. As shown in in FIG. 4, two fixation projections 56 are provided in the front area of the midsole lip 48. However, any number of fixation projections 56 may be provided, and they may be positioned at any position along the midsole lip 48.

The frame receiving portion 10 includes a plurality of portions 58, 60, and 62 corresponding to different areas of the patient's foot. For instance, a frame facing heel portion 58 of the midsole 6 corresponds to the patients heel. A frame facing midfoot portion 60 of the midsole 6 corresponds to the patient's midfoot. A frame facing forefoot portion 62 corresponds to the patient's forefoot. A bottom surface of the frame receiving portion 10 may further include a pattern defined by projections or depressions that may assist in securing the midsole 6 to the frame 4.

The midsole 6 may be made of Ethylene-vinyl acetate (EVA), or any other material that is "rubber-like" in softness and flexibility. EVA may also be referred to as expanded rubber or foam rubber. The foot receiving portion 8 and the frame receiving portion 10 are integrally molded and formed with one mold.

In use, the midsole 6 is inserted into the frame 4 such that the midsole 6 is received into and seated in the frame 4. When the midsole 6 is inserted into the frame 4, the midsole 6 and the frame 4 are secured to each other by a frictional force, i.e., secured with a snap-fit without gluing or stitching. For example, the midsole lip 48 and the frame lip 26 are configured to have corresponding contours such that when the midsole 6 is inserted into the frame 4, a snap fit is established. The contours of the frame lip 26 may mirror the contours of the midsole lip 48 such that the frame lip 26 receives and secures the midsole 6 to the frame 4.

The frictional force between the midsole 6 and the frame 4 may be aided by various features, for instance the fixation projections 56 extending from the midsole 6. When the midsole 6 is inserted into the frame 4, the fixation projections 56 are received into the side projection holes 38, ensuring a secure seating of the midsole 6 in the frame 4. Also, the ventilation portions 54 and 55 may include ribs circumscribing the ventilation portions 54 and 55 (FIG. 4C) in the midsole 6 that may be received into the ventilation holes 36 and 37 to further seat the midsole 6 in the frame 4.

Figure 5A:
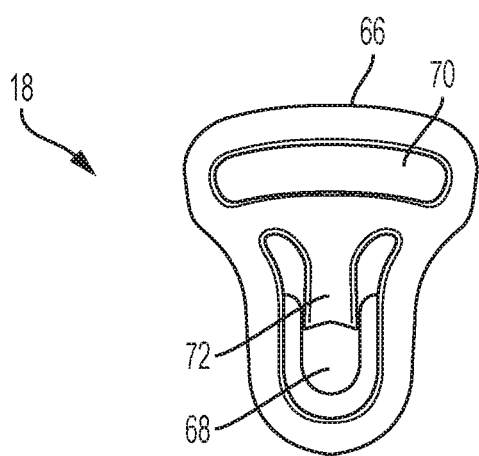
FIGS. 5A and 5B are front and back perspective views of a fixation element according to an aspect of an exemplary embodiment.
Figure 5B:
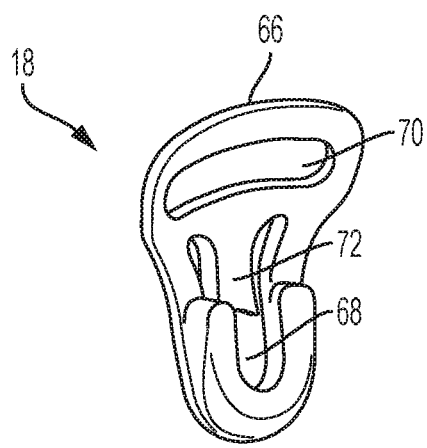

FIGS. 5A and 5B are front and back perspective views of a fixation element according to an aspect of an exemplary embodiment.

The fixation element 18 includes an exterior portion defining an outside edge of the fixation element 18, a projection through hole 68, a closure strap through hole 70, and an interior portion 72. The projection through hole 68 is a hole configured to receive one of the fixation projections 32 and 34 extending from the frame 4. The interior portion 72 is a tooth or projection that borders the projection through hole 68 and defines an edge of the projection through hole 68. The fixation elements 18 are secured to the frame 4 by inserting one of the fixation projections 32 and 34 into the projection through hole 68 of the fixation element 18. The interior portion 72 comes into contact with the fixation projection 32 or 34 and locks the fixation element 18 into place. Either of the first closure strap 14 and the second closure strap 16 may be threaded through the closure strap through hole 70 for securing the cover 12 to the fixation elements 18, and thus to the frame 4. When assembled, a fixation element 18 may be secured to each of the fixation projections 32 and 34 extending from the frame 4.

Figure 6:
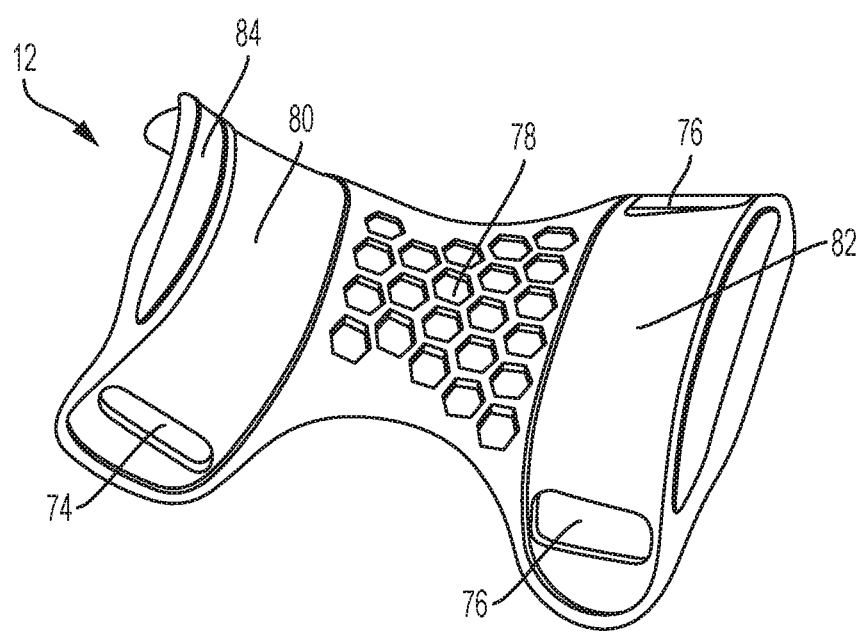
FIG. 6 is a side elevation view of a removable cover according to an aspect of an exemplary embodiment.

FIG. 6 is a side elevation view of a cover according to an aspect of an exemplary embodiment.

Typically, shoes include an upper stitched or otherwise permanently attached to the outsole of the shoe. However, the medical shoe 2 disclosed herein does not require an upper, and instead may have a removable cover 12 that is configured to secure the medical shoe 2 to the patient's foot. The removable cover 12 allows for easy access to the patient's foot, is easily removable and permits easy insertion of the patient's foot into the medical shoe, and eliminates the buckle pressure of traditional shoe securing elements. The cover 12 may be configured to substantially match the contours of the top of the patient's foot, and may include a first closure strap through hole 74 and a second closure strap through hole 76. The cover 12 is secured to the frame 4 via the first closure strap 14, the second closure strap 16, the first closure strap through hole 74, and the second closure strap through hole 76. For instance, the first 14 and second 16 closure straps are threaded through the first 74 and second 76 closure strap through holes, and are secured to a closure strap through hole 70 in a corresponding fixation element 18.

The cover 12 may further include various impressions and indentations in the surface of the cover 12 for added functionality. For instance, the cover 12 further includes a ventilation portion 78 comprising holes formed in the body of the cover 12 in between the first 74 and second 76 closure strap through holes. Thus, when the patient's foot is inserted in the assembled medical shoe 2, the ventilation portion provides ventilating air to the foot of the patient.

The cover 12 may also include depressions formed on the surface of the cover 12 for receiving and positioning the closure straps 14 and 16. For instance, a first closure strap receiving portion 80 and a second closure strap receiving portion 82 for positioning the first 14 and second 16 closure straps are provided on the surface of the cover 12. When the first closure strap 14 is threaded into the first closure strap through hole 74, the first closure strap 14 is received into the first closure strap receiving portion 80 so that the first closure strap 14 does not slide out of position on the face of the cover 12. Similarly, when the second closure strap 16 is threaded into the first closure strap through hole 76, the second closure strap 16 is received into the second closure strap receiving portion 82 so that the second closure strap 16 is secured in place with respect to the cover 12. The cover 12 may also include a cover nameplate 84 for placing advertisements, trademarks, logos, or the like.

In use, the cover 12 is easily separable from the medical shoe 2 using the first 14 and second 16 closure straps. For instance, the first 14 and second 16 closure straps can be unfastened, and the cover 12 can be removed by pulling the cover 12 straight up in a direction away from the midsole 6. This removable cover 12 provides multiple advantages, for example, the ability to secure the cover 12 to the frame 4 after the patient's foot has been received into the midsole 6. In the alternative, the cover 12 may be secured to the frame 4 prior to the patient's foot being received into the midsole 6.

Figure 7:
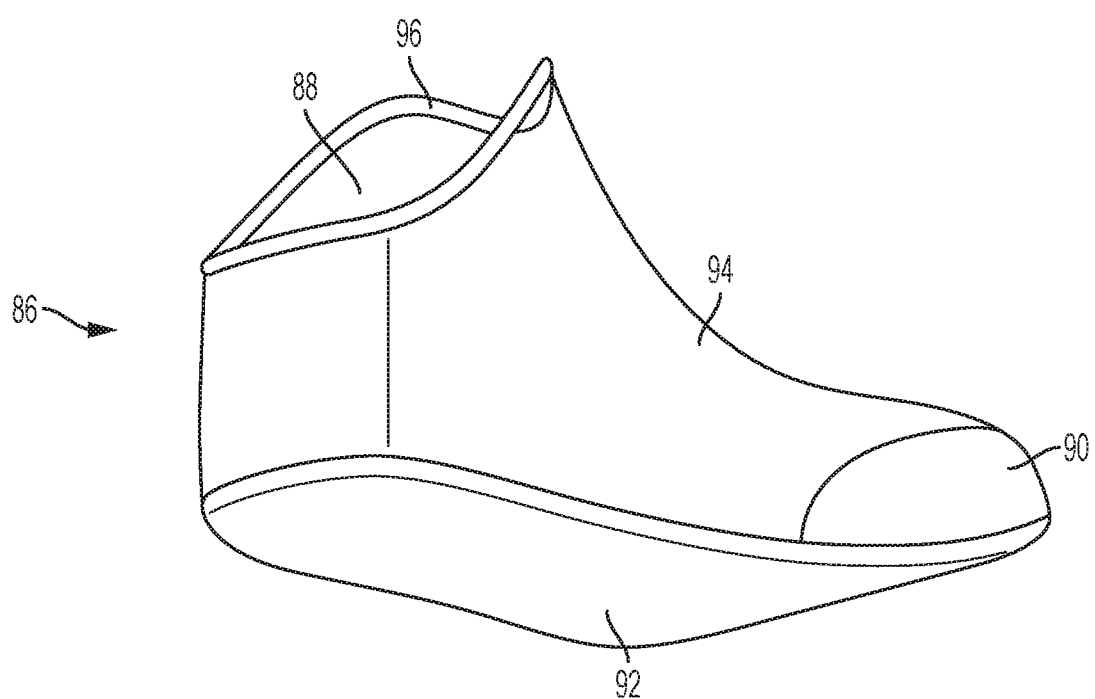
FIG. 7 is a side perspective view of a liner according to an exemplary embodiment.

FIG. 7 is a side perspective view of a liner according to an exemplary embodiment.

A liner 86 may be optionally inserted into the cavity of the medical shoe 2. The liner 86 includes an ankle portion 88, a forefoot portion 90, a foot supporting portion 92, and a body portion 94. The liner 86 may be inserted into the medical shoe 2 such that the forefoot portion 90 corresponds to the forefoot opening 22, the ankle portion 88 corresponds to the ankle opening 20, the body portion 94 corresponds to the midfoot opening 24, and the foot supporting portion 92 corresponds to the foot supporting portion 52. The liner 86 may be inserted into the medical shoe 2 before or after the removable cover 12 is secured to the frame 4 via the first 14 and second 16 closure straps.

The liner 86 may further include an ankle portion rib 96 around a circumference of the ankle portion 88 to ensure proper seating of the liner 86 in the medical shoe 2. For instance, when the liner 86 is inserted into the medical shoe 2, the ankle portion rib 96 may abut an edge of the ankle opening 20 when the liner 86 is properly seated in the medical shoe 2.

Figure 8:
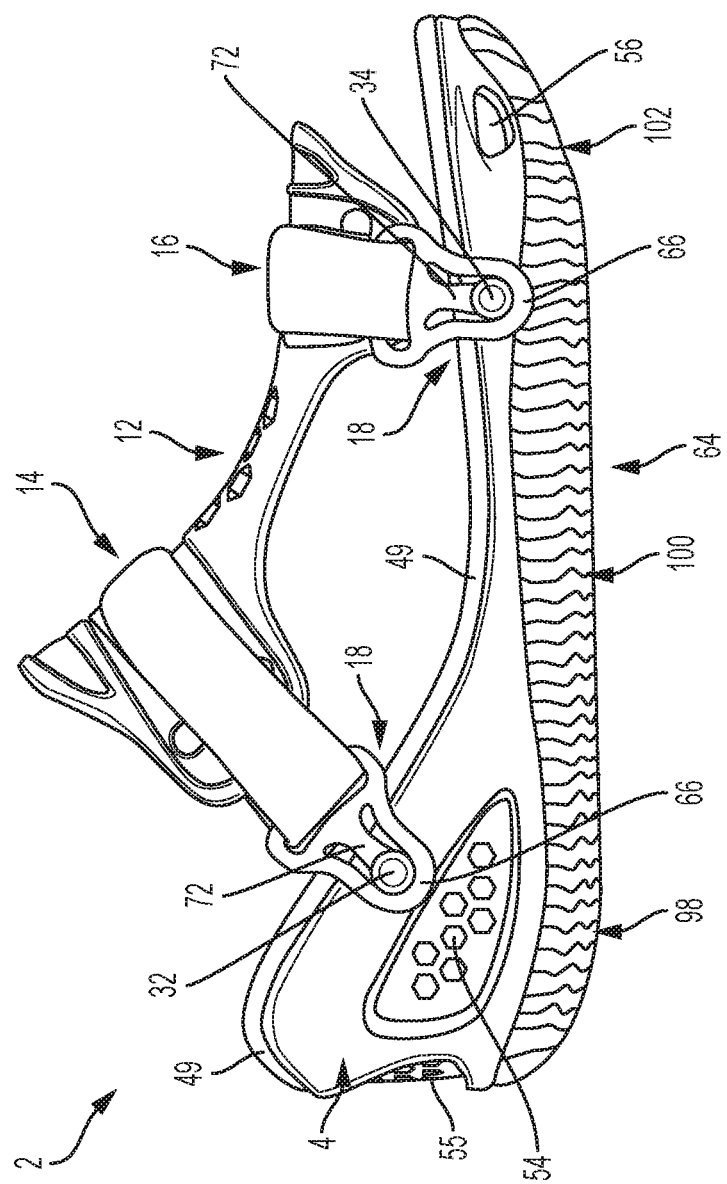
FIG. 8 is a side perspective view of a medical shoe having multi-density overmolding according to an aspect of an exemplary embodiment.
Figure 9:
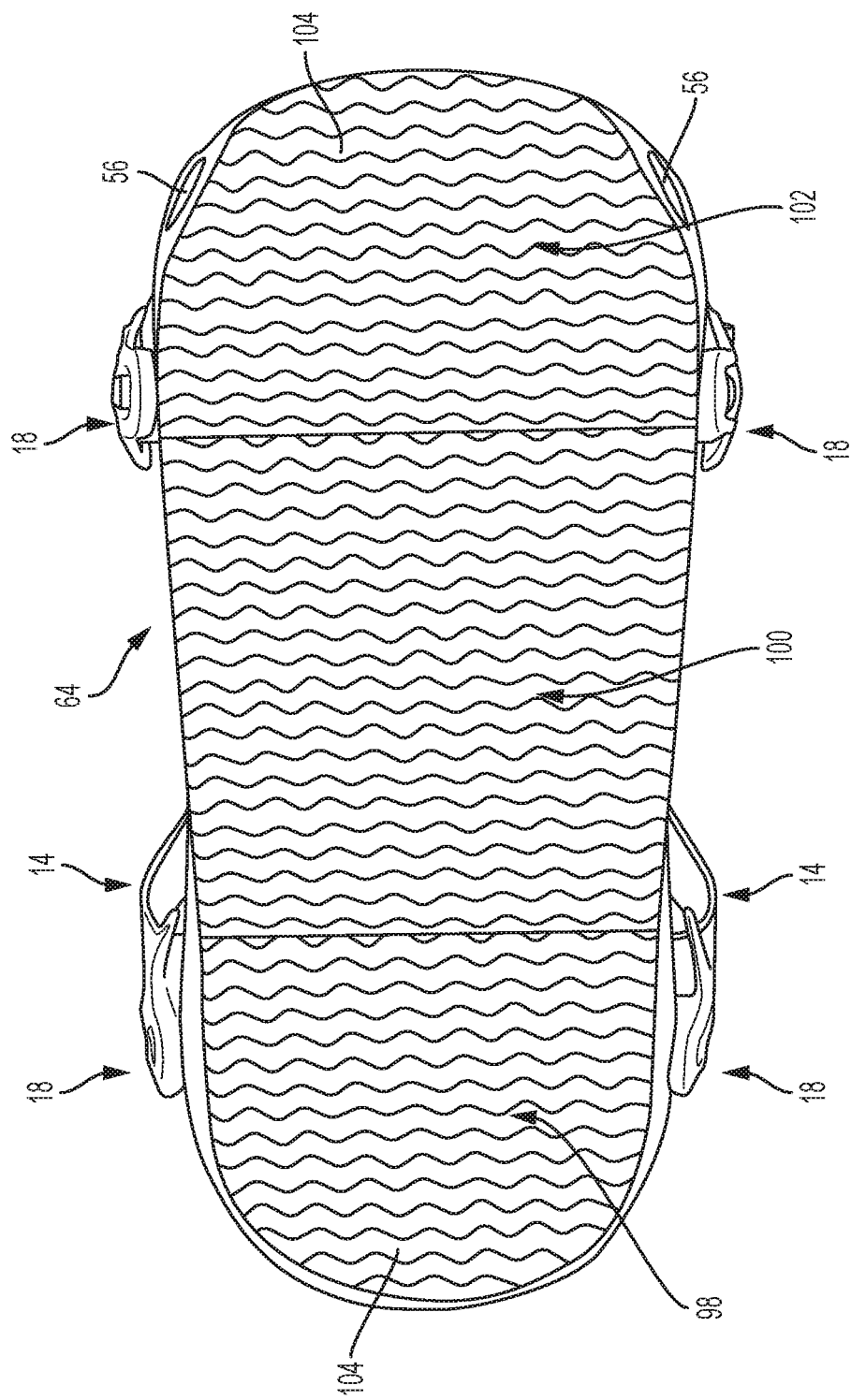
FIG. 9 is a side perspective view of a medical shoe having multi-density overmolding according to an aspect of an exemplary embodiment.

FIGS. 8 and 9 are side perspective views of a medical shoe having multi-density EVA overmolding according to an aspect of an exemplary embodiment.

Each of the frame facing heel portion 58, the frame facing midfoot portion 60, and frame facing forefoot portion of the midsole 6 correspond to a particular area of the foot, i.e., the heel, the midfoot, and the forefoot, respectively. Accordingly, each of the heel, the midfoot, and the forefoot area of the patient's foot may therefore be isolated and treated individually via the overmolding layer 64. That is, respective regions 98, 100, and 102 of the overmolding layer 64 may be designed to isolate particular regions of the foot, and may treat each region of the foot depending on a desired off-loading scenario. In other words, each of the overmolding heel portion 98, overmolding midfoot portion 100, and overmolding forefoot portion 102 can be designed and/or modified to address a desired weight distribution across the patient's heel, midfoot, and forefoot depending on a condition of the patient's heel, midfoot, and forefoot.

Different offloading scenarios may be achieved by constructing the overmolding layer 64 of materials having varying densities. By utilizing multi-density materials, for example multi-density EVA foam, area specific pressure reduction can be achieved by strategic placement of low-density materials and high-density materials.

For example, depending on the patient's medical condition, it may be desirable to off-load pressure from the patient's heel by shifting weight to the midfoot and forefoot areas, for instance to promote faster healing after surgery, trauma, or when wounds or ulcerations are present on the heel. Thus, the medical shoe 2 may be configured for off-loading weight from the patient's heel and shifting the weight to the midfoot and forefoot areas of the patient's foot. Such an off-loading configuration may be desirable in cases of rear foot trauma, wounds or ulcerations present on the heel area, and post-surgical healing for either soft tissue or bony structure of the heel.

In this configuration, the medical shoe 2 includes an overmolding heel portion 98 have a density less than that of the overmolding midfoot portion 100 and the overmolding forefoot portion 102. The overmolding heel portion 98 has reduced density such that the weight of the patient is off-loaded from the heel area of the patient's foot and is distributed across the patient's midfoot and forefoot areas.

In the alternative, in some instances, it may be desirable to reduce weight bearing pressure on the patient's forefoot to promote faster healing after surgery, trauma, or when forefoot wounds or ulcerations are present. Thus, the medical shoe 2 may be configured for off-loading weight from the patient's forefoot and shifting the weight to the midfoot and heel area.

In this configuration, the medical shoe 2 includes an overmolding forefoot portion 102 having a density less than that of the overmolding heel portion 98 and the overmolding midfoot portion 100. The overmolding forefoot portion 102 has reduced density such that the weight of the patient is off-loaded from the forefoot area of the patient's foot and is distributed across the patient's midfoot and heel areas.

According to another aspect of an exemplary embodiments, each of the overmolding portions 98, 100, and 102 may have an independently determined density so as to create a customized off-loading scenario, for example, designed for a specific patient. That is, each of the overmolding portions 98, 100, and 102 may have the same or a different density, and the densities of each of the overmolding portions 98, 100, and 102 may be determined individually so as to create a customized off-loading scenario based on a particular desired off-loading effect. By decreasing the relative density of each of the overmolding portions 98, 100, and 102, a greater off-loading effect may be achieved with respect to the adjacent portion of the patient's foot.

One or more of the overmolding portions 98, 100, and 102 may optionally include contouring 104, as illustrated in FIG. 9, at the ground contacting surface. Thus, the ground contacting surfaces of each of the overmolding portions 98, 100, and 102 may include one of either of a low traction ground contact tread or a high traction ground contacting tread 108. The contouring 104 may have varying levels of increased traction, and thus may be used to create zones of increased traction under each of the overmolding portions 98, 100, and 102 when increased traction is required.

According to an aspect of an exemplary embodiment, the midsole 6 may be a patient specific midsole. In this case, the midsole may be designed according to a specific patient's needs or based off data received from a patient. The data may include foot data, including the size, shape, and/or curvature of the patient's foot. In this case, the foot receiving portion 8 of the midsole 6 may be tailored to the size and curvature of the patient's foot. The foot data may include an image scan, a CT scan, and MRI scan, a mold, or a combination thereof.

The data may also include patient data, i.e., information about a condition of the patient, for instance whether the patient has experienced one or more of surgery of the foot, trauma of the foot, a wound of the foot, or an ulceration of the foot. In this case, the overmolding layer 64 may be designed based on the condition of the patient to achieve a therapeutic weight distribution across the patient's foot. The patient data may include data from medical records, data received from a medical database, or data received from a medical professional.

In the alternative, the midsole 6 may not be patient specific, and instead may be made without consideration of data from a specific patient. In this case, the midsole 6 may be provided in varying sizes, and the patient may be provided with a midsole 6 that most closely matches the size of the patient's foot.

The frame 4 may or may not be patient specific depending on the structure of the midsole 6. It is contemplated that the frame 4 is designed to be interchangeable with the various configurations of the midsole 6. For instance, even if a midsole 6 is specially designed to accommodate a larger foot, i.e., by increasing the size of the foot bed, the midsole 6 may still be designed to be received into the frame 4 having a standardized size.

Figure 10A:
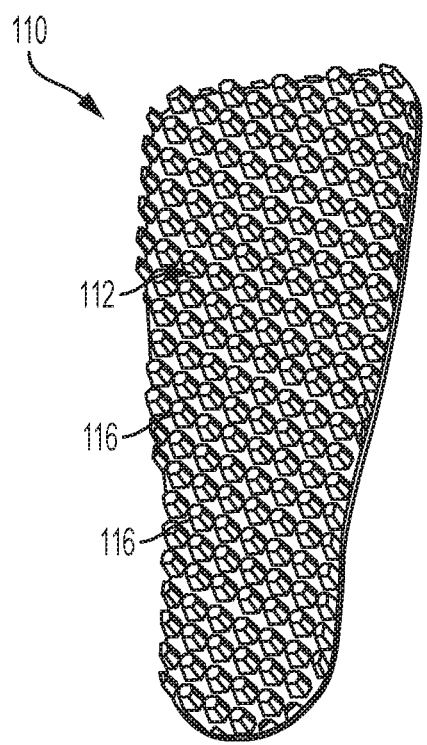
FIGS. 10A and 10B are front and back perspective views of a removable insole according to an aspect of an exemplary embodiment.
Figure 10B:
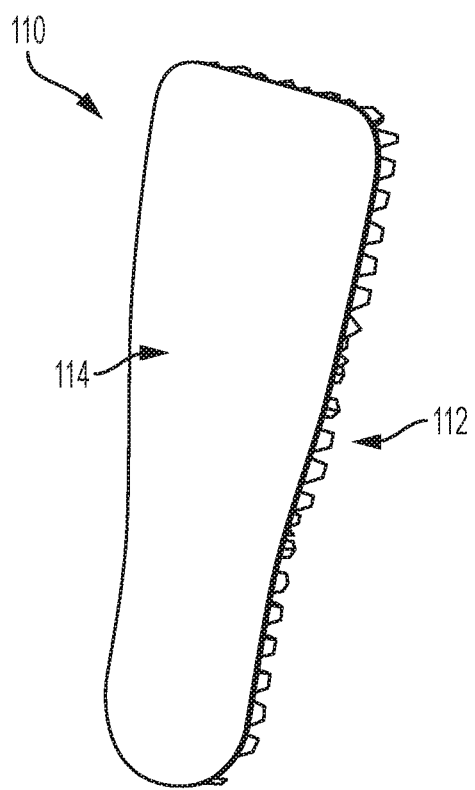

FIGS. 10A and 10B are front and back perspective views of a removable insole according to an aspect of an exemplary embodiment.

The removable insole 110 includes a midsole portion facing side 112 and a foot receiving side 114. The removable insole 110 is configured to be inserted into the medical shoe 2 such that the midsole portion facing side 112 faces the foot receiving portion 8 of the midsole 6, and more specifically the foot supporting portion 52, and such that the foot receiving side 114 faces up towards the cover 12 in order to receive and support the patient's foot.

The removable insole 112 further includes pressure distribution pegs 116 on the midsole portion facing side 112 that provide customizable targeted off-loading of the patient's foot. By adjusting the relative lengths of the pressure distribution pegs 116, weight may be off-loaded from targeted areas of the patient's foot. For instance, pressure distribution pegs 116 adjacent to an injured area of the patient's foot may be made shorter than pressure distribution pegs 116 adjacent to non-injured areas of the patient's foot. Thus, weight can be off-loaded from the injured area of the patient's foot to the non-injured areas of the patient's foot.

Figure 11:
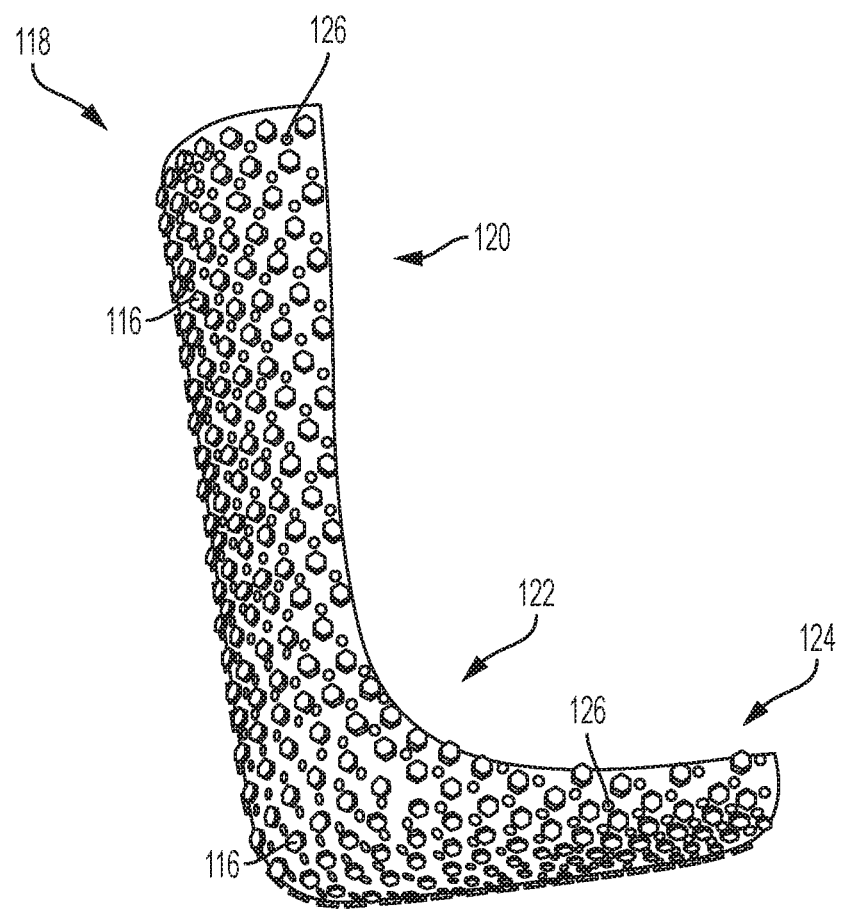
FIG. 11 is a side perspective view of an ankle liner according to an aspect of an exemplary embodiment.

FIG. 11 is a side perspective view of an ankle liner according to an aspect of an exemplary embodiment.

Similar to the removable insole of FIGS. 10A and 10B, an ankle liner 118 may be used for targeted off-loading of the patient's foot and ankle. The ankle liner 118 includes an ankle portion 120, a heel portion 122, and a foot portion 124. The ankle liner 118 is configured to be inserted into the medical shoe 2, and to provide support to the ankle, heel and foot areas of the patient. Thus, the ankle liner 118 extends from the patient's ankle to the patient's forefoot.

The ankle liner 118 also includes the pressure distribution pegs 116 to provide customizable targeted off-loading from patient's ankle, heel, midfoot, and forefoot. By adjusting the relative lengths of the pressure distribution pegs 116, weight may be off-loaded from targeted areas of the patient's ankle and foot.

The ankle liner 118 further includes ventilation holes 126 for providing ventilated air to areas of the patient's ankle and foot. Thus, even when the patient's foot is received into the assembled medical shoe, ventilating air may be provided through the ventilation holes in the ankle liner 118.

Figure 12A:
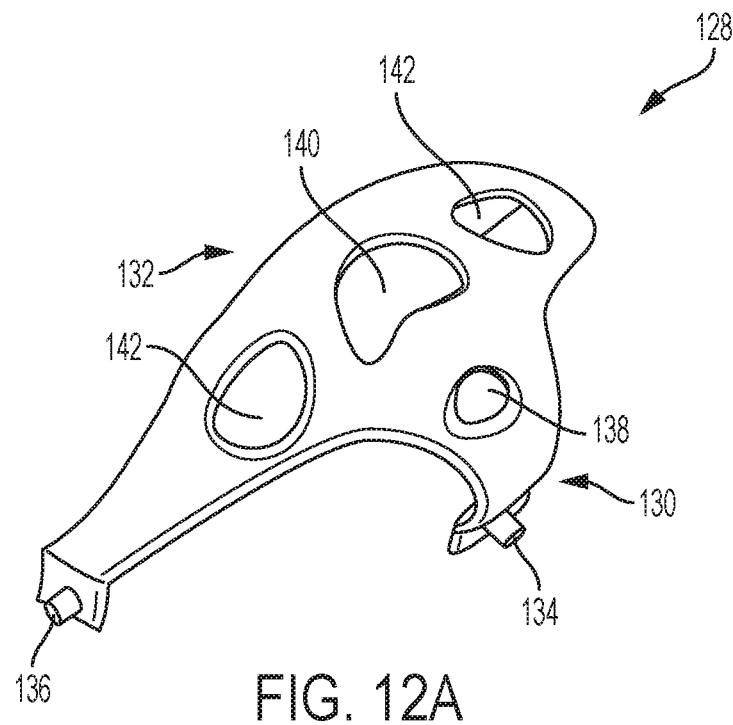
FIGS. 12A and 12B are front and back perspective views of a removable toe cover according to an aspect of an exemplary embodiment.
Figure 12B:
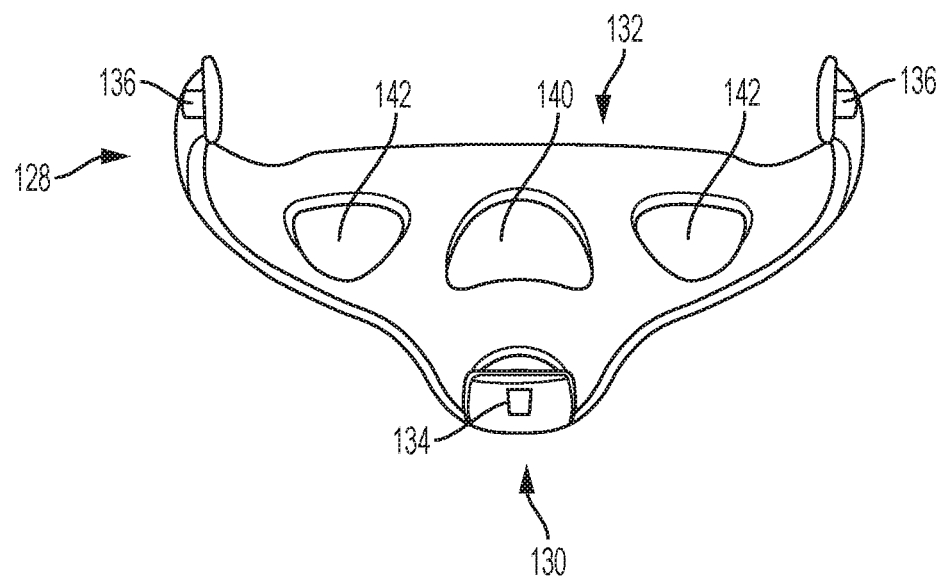
Figure 13:
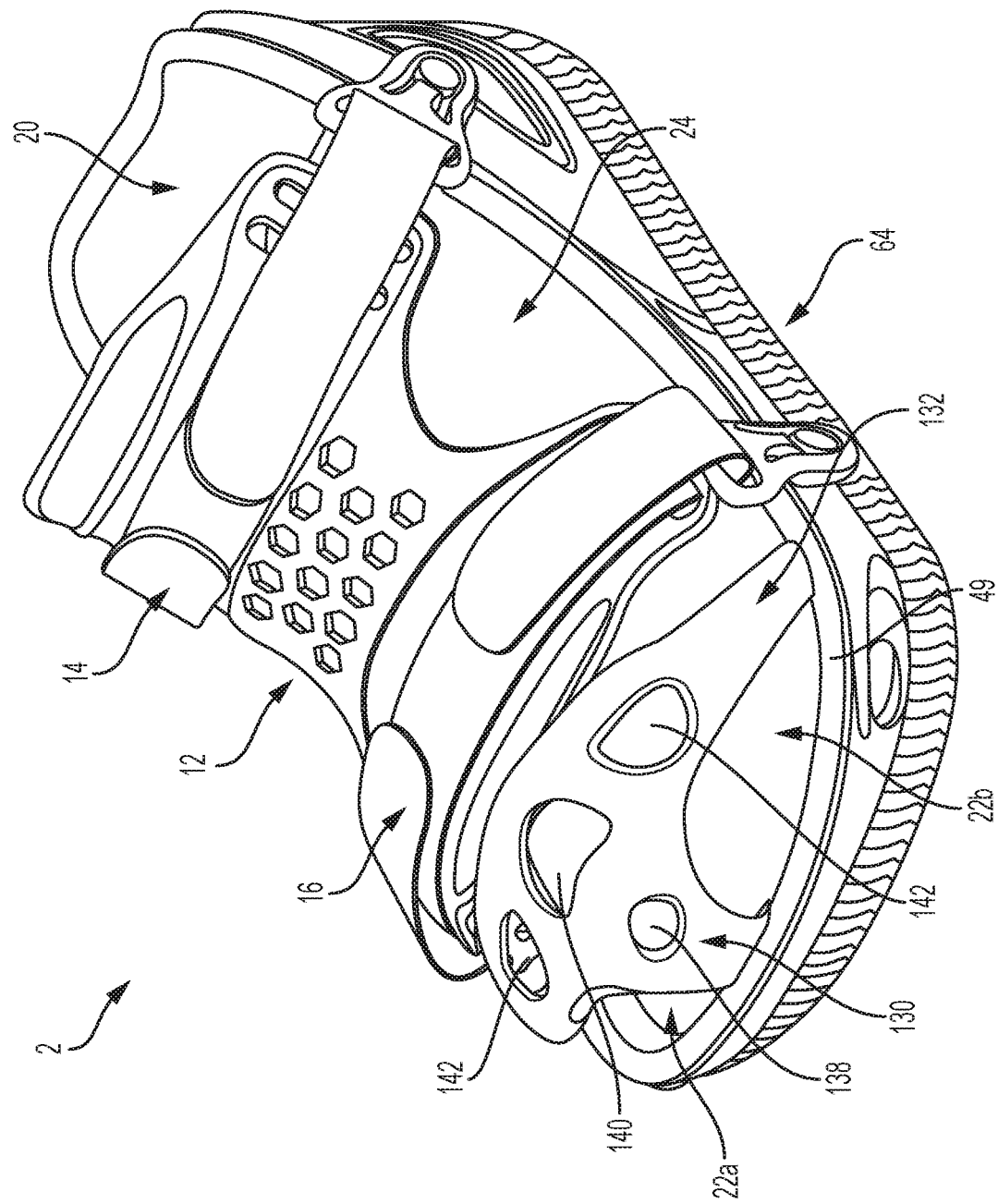
FIG. 13 is a side perspective view of a medical shoe having a removable toe protector according to an aspect of an exemplary embodiment.

FIGS. 12A and 12B are front and back perspective views of a removable toe cover according to an aspect of an exemplary embodiment. FIG. 13 is a side perspective view of a medical shoe having a removable toe protector according to an aspect of an exemplary embodiment.

The medical device 2 may include a detachable toe protector 128 for use when the patient has a wound or other trauma to the toes or front forefoot area. For example, the detachable toe protector 128 may protect the patient's toes and front forefoot area from foreign objects that may agitate or worsen the traumatized region while promoting easy visual inspection thereof.

The toe protector includes two elongated portions, i.e., an anterior portion 130 and a dorsal portion 132. The anterior portion 130 extends from a central area of the dorsal portion 132 in a direction substantially perpendicular to the dorsal portion 132, so as to form a protective guard. The anterior portion 130 and the dorsal portion 132 may also be curved so as to form a cup shape.

The toe protector 128 may include fixation elements 134 and 136 for detachably fixing the toe protector to the medical shoe 2. The fixation elements may include a nub or protrusion extending from a surface of the toe protector 128. However, the exemplary embodiments are not limited thereto, and any fixation element known to provide a detachable connection may be provided, including snaps, magnetic connectors, or the like. An anterior fixation element 134 may be located at an end of the anterior portion 130 opposite the side that the anterior portion 130 is joined to the dorsal portion 132. The dorsal portion 132 may include dorsal fixation elements 136 on both ends thereof.

The toe protector 128 may include holes in the body thereof for promoting easy visual inspection of, as well as for providing a circulating air current to, the patient's toe and front forefoot region. For example, the toe protector 128 may include an anterior hole 138 centrally located in the anterior portion 130. The toe protector 128 may further include a dorsal center hole 140 centrally located in the dorsal portion 132. The dorsal center hole 140 may be surrounded on either side by dorsal side holes 142.

When fixed to the medical shoe 2, as shown in FIG. 13, the toe protector 138 may be received into the midsole 6 via the fixation elements 134 and 136 so as to form a protective guard above the forefoot opening 22. For instance, the midsole 6 may include a receiving portions (not shown) for receiving the fixation elements 134 and 136 and fixing the toe protector 128 to the midsole 6. The receiving portions may include corresponding holes, snaps, or magnetic connectors corresponding to the fixation elements 134 and 136.

The dorsal portion 132 may be positioned across the medical shoe 2 in a direction perpendicular to the patient's foot, i.e., parallel to the first closure strap 14 and the second closure strap 16. The anterior portion 130 may be positioned to extend from the dorsal portion 132 in a direction parallel to the patient's foot, i.e., perpendicular to the first closure strap and the second closure strap. In this configuration, the toe protector 128 substantially fills and protects the patient's foot in the area of the forefoot opening 22. Additionally, the anterior portion 130 bisects the forefoot opening into a first forefoot opening 22a and a second forefoot opening 22b, such that easy visual inspection is maintained.

The toe protector 128 may be made of the same material as the midsole 6, for instance, EVA foam, or may be made of a different material suitable for providing protection to the foot. The toe protector 128 is preferably made of a rigid material that is also lightweight and flexible for promoting the patient's comfort, including plastic, polystyrene, expanded polystyrene (EPS), lightweight metals, fiberglass, and the like.

While one or more exemplary embodiments have been described with reference to the figures, it will be understood by those of ordinary skill in the art that various changes in form and details may be made therein without departing from the spirit and scope as defined by the following claims.

What is claimed is:

1. A medical shoe comprising:
   a midsole configured to support a foot, the midsole comprising:
     a foot receiving portion forming a substantially planar surface for supporting the foot; and
     a frame receiving portion opposite the foot receiving portion;
   a frame surrounding the midsole, the frame comprising a plurality of through holes, and
   an overmolding layer extending from a side of the frame opposite the midsole so as to form a ground contacting surface,
   wherein the overmolding layer has a non-uniform density, and
   wherein the midsole is secured to the frame by a self-locking fit between the midsole and the frame.

2. The medical shoe of claim 1, wherein:
   the midsole further comprises a midsole lip portion extending around a circumferential edge of the midsole in a direction perpendicular to the substantially planar surface,
   the frame further comprises a frame lip portion surrounding the midsole lip portion such that a contour of an inner surface the frame lip portion corresponds to a contour of an outer surface the midsole lip portion, and
   the self-locking fit comprises a frictional force between the midsole and the frame.

3. The medical shoe of claim 2, wherein:
   the midsole further comprises a fixation projection extending from the midsole lip portion in a direction parallel to the substantially planar surface,
   the frame further comprises a fixation projection through hole in the frame lip portion, and
   the fixation projection extends into the fixation projection through hole.

4. The medical shoe of claim 1, wherein:
   the overmolding layer comprises a rear heel portion, a midfoot portion, and a front forefoot portion;
   the front forefoot portion has a first density;
   the rear heel portion has a second density different than the first density; and
   the midfoot portion has a third density equal to one of the first density and the second density.

5. The medical shoe of claim 4, wherein the first density is greater than the second density.

6. The medical shoe of claim 4, wherein the second density is greater than the first density.

7. The medical shoe of claim 4, wherein the midsole is composed of ethylene-vinyl acetate.

8. The medical shoe of claim 4, wherein the overmolding layer comprises a tread pattern formed therein on the ground contacting surface.

9. The medical shoe of claim 1, further comprising a removable cover secured to the frame and located above the midsole, such that a cavity configured to surround the foot is defined by a bottom surface of the removable cover and a top surface of the midsole.

10. The medical shoe of claim 9, further comprising a fixation element and a closure strap, wherein:
the fixation element is secured to a fixation projection extending from the frame and comprises a fixation element slot configured to receive the closure strap;
the removable cover comprises a removable cover slot configured to receive the closure strap, and
the closure strap is positioned through the fixation element slot and through the removable cover slot.

11. The medical shoe of claim 9, further comprising ventilation holes formed in the removable cover.

12. The medical shoe of claim 1, further comprising a removable insole located on the substantially planar surface, the removable insole comprising:
a foot supporting portion; and
a plurality of pressure distribution pegs extending from the food supporting portion towards the substantially planar surface,
wherein the plurality of pressure distribution pegs are non-uniform in height.

13. A snap fit medical shoe assembly, comprising
a midsole configured to support a foot, the midsole comprising:
a foot receiving portion forming a substantially planar surface for supporting the foot;
a frame receiving portion opposite the foot receiving portion; and
a midsole lip portion extending around a circumferential edge of the midsole in a direction perpendicular to the substantially planar surface;
a rigid exoskeleton configured to surround the midsole, the rigid exoskeleton comprising:
an exoskeleton lip portion corresponding to the midsole lip portion; and
an ethylene-vinyl acetate overmolding layer extending from a side of the rigid exoskeleton opposite the midsole so as to form a ground contacting surface; and
a removable cover configured to be secured to the rigid exoskeleton,
wherein the ethylene-vinyl acetate overmolding layer has a non-uniform density, and
wherein a contour of an inner surface the exoskeleton lip portion corresponds to a contour of an outer surface the midsole lip portion, such that the midsole is configured to be secured to the rigid exoskeleton by a snap fit between the midsole and the rigid exoskeleton.

14. The snap fit medical shoe assembly of claim 13, wherein:
the ethylene-vinyl acetate overmolding layer comprises a rear heel portion, a midfoot portion, and a front forefoot portion;
the front forefoot portion has a first density;
the rear heel portion has a second density different than the first density; and
the midfoot portion has a third density equal to one of the first density and the second density.

15. The medical shoe of claim 14, wherein the first density is greater than the second density.

16. The medical shoe of claim 14, wherein the second density is greater than the first density.

17. A method of attaching orthopedic bracing, the method comprising:
providing a midsole configured to support a foot of a patient, the midsole comprising:
a foot receiving portion forming a substantially planar surface for supporting the foot; and
a frame receiving portion opposite the foot receiving portion,
providing a rigid exoskeleton, the rigid exoskeleton comprising an overmolding layer having a non-uniform density,
positioning the midsole into an interior of the rigid exoskeleton such that the midsole is secured to the rigid exoskeleton by a snap fit between the midsole and the rigid exoskeleton;
positioning the substantially planar surface adjacent to a bottom portion of the foot of the patient; and
positioning a removable cover adjacent to a top portion of the foot of the patient foot and securing the removable cover to the rigid exoskeleton.

18. The method of claim 17, wherein the midsole is provided differently depending on the foot of the patient and a medical condition of the patient, such that the non-uniform density is provided in one of different manners depending on the medical condition of the patient.

19. The method of claim 18, wherein the providing the rigid exoskeleton comprises providing a rigid exoskeleton independent of the different manners in which the non-uniform density is provided.

20. The method of claim 18, wherein the non-uniform density is provided in the one of the different manners depending on whether the medical condition of the patient is one of: surgery of the foot, trauma of the foot, a wound of the foot, and an ulceration of the foot.

21. A medical shoe comprising:
a midsole configured to support a foot;
a frame surrounding the midsole; and
an overmolding layer extending from the frame so as to form a ground contacting surface,
wherein the overmolding layer has a non-uniform density, and
wherein the midsole is secured to the frame by a snap fit between the midsole and the frame.

* * * * *